Nov. 5, 1935. L. C. BOBBINK Plant Pat. 145
AZALEA
Filed May 29, 1935
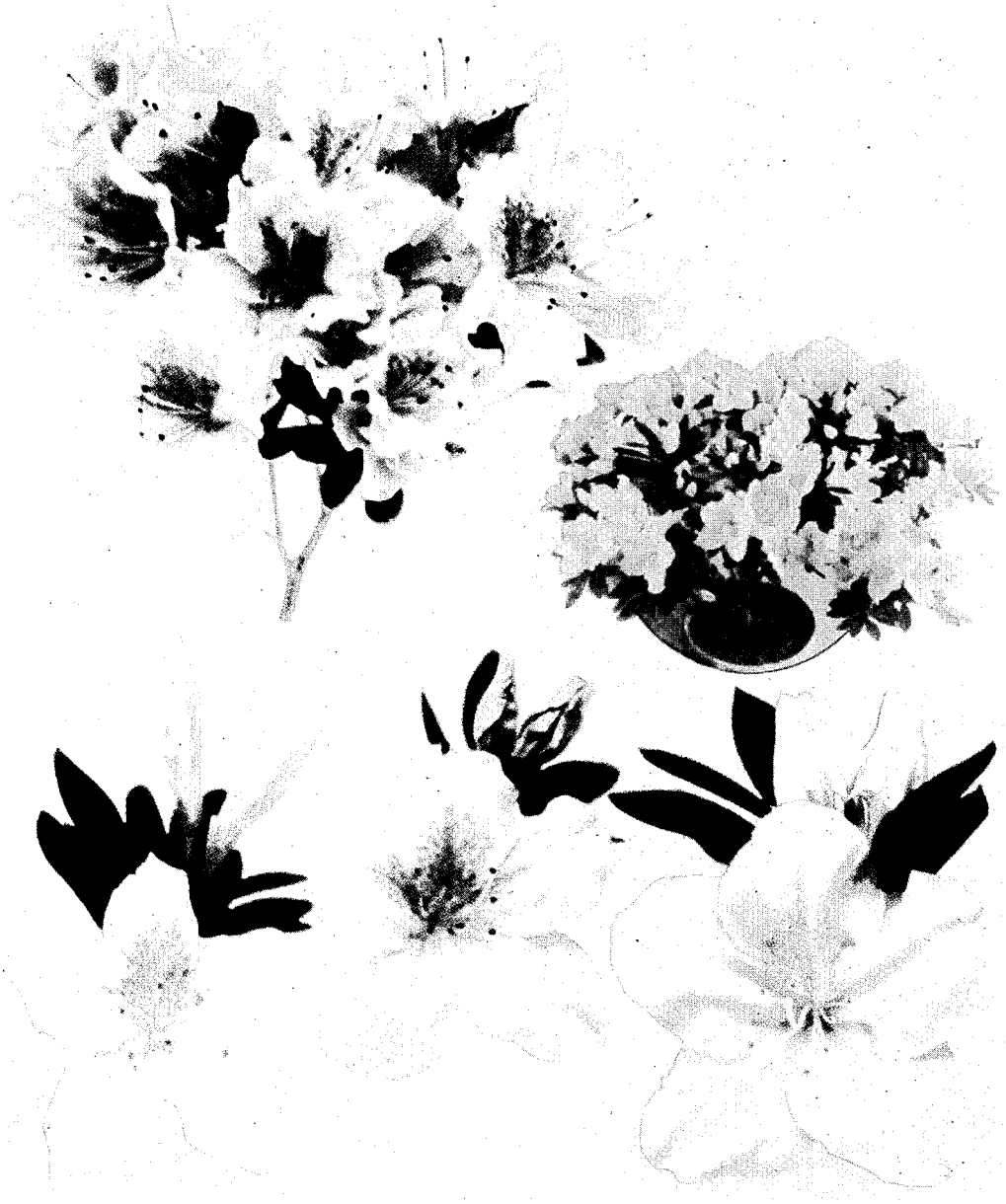
INVENTOR
Lambertus Christian Bobbink
By Orville M. Kile
PLANT PATENT AGENT Patented Nov. 5, 1935

Plant Pat. 145

UNITED STATES PATENT OFFICE

145

AZALEA

Lambertus Christian Bobbink,
East Rutherford, N. J.

Application May 29, 1935, Serial No. 24,131

1 Claim. (Cl. 47—60)

My invention consists of a distinct improvement in azaleas of the type known as tender or greenhouse evergreen forcing. These new azaleas were produced through a long series of cross breeding involving principally the crossing of the Japanese Kurume azalea with the Indica or Belgian forcing azalea, but involving also the injection of rhododendron blood.

These plant breeding and selecting efforts extending over the past ten years have developed a distinct new type of azalea, differing in many important respects from any of the parent types, and in general combining the large flowers of Indica with the graceful form and floriferousness of the Kurume, but being much more rapid in growth and freer of flowering than either.

I have developed this new type or race of azaleas into three separate and distinct varieties notably differentiated by petal formation and arrangement; namely, single, double and semi-double—the latter generally known as hose-in-hose.

The subject of my present invention is the "single" variety of this new type of azalea. This variety was produced as follows: *Indica alba,* or more properly *Ledifolia alba,* a large flowered single white, was crossed with Omursaki, an exceptionally large single Kurume variety, purplish-wine in color, flowering in truss formation and of very vigorous growth. This cross produced some light lilac flowering plants from which the best were selected and crossed with the Indica variety Mme. Petrick. This produced a pink with a lavender sheen, and the best plant of this lot that showed good foliage, the truss flowering habit and vigorous growth, was then crossed with Rhododendron Pink Pearl. This cross apparently gave a larger flower of paler pink, but the foliage was not satisfactory. This was then crossed with the variety Single Macrantha to improve the foliage. This resulted in a much more compact plant with excellent foliage, rose pink in color and blooming in trusses. With this original variety established, sub-varieties or variations in desired colors are readily secured by well known horticultural methods.

The accompanying illustration shows a typical cluster or truss of flowers fully opened, three typical individual flowers with buds and leaves—all in full color and approximately natural size in the original paintings—and at the upper right a small view in black and white of a small potted plant of this variety.

The following is a detailed description of this variety.

*The plant.*—Grows rapidly, usually nearly twice as fast as the Indicas and produces salable flowering plants in two years as contrasted with the usual three to four years required for Indica. Some of the sub-varieties of this variety bloom well in advance of the Christmas market while others bloom as late as the end of May—long after Indicas cease blooming.

This variety can be readily grown on its own roots and does not require grafting as is the case with most Belgian Indicas. The rooted plants form an excellent "ball"—so desirable for distant transportation and transplanting.

The form of the plant is bushy but graceful and spreading, forming a solid mass of blossoms when the plant has attained several years' growth.

This variety is hardy in the southern tier of States—Georgia, Alabama, Mississippi, South Carolina and similar latitudes.

Truss formation.—An important and distinctive feature is the so-called truss structure or formation of the flowering branches. This many-branched structure is similar to that of the American rhododendron. Each branch sends out each year from its terminal bud 3 to 5 or sometimes as many as 7 branches. These branches are relatively short and thus the plant as a whole acquires, after a few years, a very compact and dense growth over its surface area. Each new branch bears at its terminal bud a group of 6 to 12 leaves and 3 to 5 flowers. The result of this peculiar growth habit is that when the large flowers are in bloom the surface and sides of the plant present to the eye a solid mass of color. Each flower crowds its neighbor so closely that very little foliage is visible.

Foliage.—Evergreen; the new growth is light green while the old growth, which is the foliage in view when the plants are in bloom, is quite dark green in color.

The individual leaves are small, somewhat spatulate in shape and of greatly varying lengths in the same cluster, but seldom more than 2 inches long. Taken together, however, the foliage is plentiful and where visible it forms a contrasting background for the blossoms. When not in bloom this rich dark green foliage provides a pleasing decorative plant. The older leaves drop off gradually during their second year but are constantly replaced by newer leaves.

*Flowers.*—Very large, measuring in some sub-varieties 3 to 3½ inches across and in nearly all sub-varieties at least 2½ inches. This variety has five petals with somewhat curling and frilled edges. One of the petals is heavily flecked with small, dark spots and the adjacent petal on either side of this one petal is slightly flecked. These five petals are joined into a closed tube or corolla ½ to ⅔ the distance toward their base.

Stamens are few, long and tipped with prominent anthers. The style usually protrudes prominently even beyond the anthers.

The flowers either have been or may be produced, by well known horticultural methods, in all colors and shades ranging from white to dark carmine and including lilac, lavender, mauve and purple, also in combinations of colors.

The flowers remain fresh and beautiful on the plant for an extremely long time, in fact about twice as long as the Indicas which are at present used by florists for forcing. Six to seven weeks of good bloom are common under ordinary conditions and the period may be lengthened by keeping the plants cool.

Having thus disclosed my invention, I claim:

The variety of evergreen azalea herein described and illustrated characterized particularly by the quick graceful growth and early and profuse flowering of the plant in trusses, by the production of flowers of very large size, of single, five-petalled structure, with sub-varieties blooming over an exceptionally wide range of time and in colors ranging from white to dark carmine.

LAMBERTUS CHRISTIAN BOBBINK.